US010143661B2

(12) United States Patent
Sandford

(10) Patent No.: US 10,143,661 B2
(45) Date of Patent: Dec. 4, 2018

(54) MALIC ACID STABILIZED NANOCERIA PARTICLES

(71) Applicant: Cerion, LLC, Rochester, NY (US)

(72) Inventor: David Wallace Sandford, Rochester, NY (US)

(73) Assignee: Cerion, LLC, Rochester, NY (US)

( * ) Notice: Subject to any disclaimer, the term of this patent is extended or adjusted under 35 U.S.C. 154(b) by 0 days.

(21) Appl. No.: 15/029,672

(22) PCT Filed: Oct. 17, 2014

(86) PCT No.: PCT/US2014/061044
§ 371 (c)(1),
(2) Date: Apr. 15, 2016

(87) PCT Pub. No.: WO2015/058037
PCT Pub. Date: Apr. 23, 2015

(65) Prior Publication Data
US 2016/0331697 A1  Nov. 17, 2016

Related U.S. Application Data

(60) Provisional application No. 61/961,525, filed on Oct. 17, 2013.

(51) Int. Cl.
*A61K 9/51* (2006.01)
*A61K 33/00* (2006.01)
*A61K 9/10* (2006.01)
*A61K 9/14* (2006.01)

(52) U.S. Cl.
CPC ............ *A61K 9/5192* (2013.01); *A61K 9/10* (2013.01); *A61K 9/14* (2013.01); *A61K 9/5123* (2013.01); *A61K 33/00* (2013.01)

(58) Field of Classification Search
None
See application file for complete search history.

(56) References Cited

U.S. PATENT DOCUMENTS

| | | | |
|---|---|---|---|
| 1,592,713 A | 7/1926 | Bendixen | |
| 2,965,678 A | 12/1960 | Sundberg et al. | |
| 2,965,994 A | 12/1960 | Sullivan | |
| 3,002,826 A | 10/1961 | Norris | |
| 3,951,934 A | 4/1976 | Ohshima et al. | |
| 3,964,994 A | 6/1976 | Kelly | |
| 4,061,473 A | 12/1977 | Norris | |
| 4,231,893 A | 11/1980 | Woodhead | |
| 4,294,586 A | 10/1981 | Cox | |
| 4,359,969 A | 11/1982 | Mellovist et al. | |
| 4,389,220 A | 6/1983 | Kracklauer | |
| 4,545,923 A | 10/1985 | Gradeff et al. | |
| 4,599,201 A | 7/1986 | Gradeff et al. | |
| 4,661,321 A | 4/1987 | Byrd et al. | |
| 4,744,796 A | 5/1988 | Hazbun et al. | |
| 4,786,325 A | 11/1988 | Melard et al. | |
| 5,004,478 A | 4/1991 | Vogel et al. | |
| 5,017,352 A | 5/1991 | Chane-Ching et al. | |
| 5,105,772 A | 4/1992 | Olsson et al. | |
| 5,097,090 A | 5/1992 | Beck | |
| 5,248,744 A | 9/1993 | Cramm et al. | |
| 5,344,588 A | 9/1994 | Chane-Ching | |
| 5,385,648 A | 1/1995 | Sugishima et al. | |
| 5,389,352 A | 2/1995 | Wang | |
| 5,405,417 A | 4/1995 | Cunningham | |
| 5,449,387 A | 9/1995 | Hawkins et al. | |
| 5,520,710 A | 5/1996 | Olah | |
| 5,525,249 A | 6/1996 | Kordonsky | |
| 5,552,133 A | 9/1996 | Lambert et al. | |
| 5,712,218 A | 1/1998 | Chopin et al. | |
| 5,759,917 A | 6/1998 | Grover et al. | |
| 5,906,664 A | 5/1999 | Basu et al. | |
| 5,910,466 A | 6/1999 | Yamashita et al. | |
| 5,938,837 A | 8/1999 | Hanawa et al. | |
| 6,093,223 A | 7/2000 | Lamaire et al. | |
| 6,133,194 A | 10/2000 | Cuif et al. | |
| 6,136,048 A | 10/2000 | Birchem et al. | |
| 6,158,397 A | 12/2000 | Peters et al. | |
| 6,210,451 B1 | 4/2001 | Chopin et al. | |

(Continued)

FOREIGN PATENT DOCUMENTS

| | | |
|---|---|---|
| CA | 1201128 | 2/1986 |
| CA | 2536276 A1 | 3/2005 |
| CN | 1792456 | 6/2006 |
| CN | 1887718 | 1/2007 |
| EP | 0208580 A1 | 1/1987 |
| EP | 0475620 A2 | 8/1991 |
| EP | 1842591 A1 | 10/2007 |
| FR | 2789601 A1 | 8/2000 |
| FR | 2885308 A1 | 11/2006 |
| GB | 360171 | 11/1931 |
| JP | 591439 A | 1/1984 |
| JP | 5945925 A | 3/1984 |
| JP | 05155616 A | 6/1993 |
| JP | 08509002 A | 9/1996 |
| JP | 11501609 A | 2/1999 |
| JP | 2001507739 A | 6/2001 |
| JP | 2001524918 A | 12/2001 |

(Continued)

OTHER PUBLICATIONS

Beverly A. Rzigalinski, Nanoparticles and Cell Longevity, Technology in Cancer Research & Treatment, 4(6), 651-659 (2005).

(Continued)

*Primary Examiner* — Hasan S Ahmed
*Assistant Examiner* — Randeep Singh
(74) *Attorney, Agent, or Firm* — RatnerPrestia

(57) ABSTRACT

A process for making nanoparticles of biocompatible materials is described, wherein an aqueous reaction mixture comprising cerous ion, malic acid, an oxidant, and water, is provided along with temperature conditions to directly form within the reaction mixture, a stable dispersion of nanoceria particles. Biocompatible nanoparticles comprised of ceria and malic acid are described. A reduction in cell death in a murine model of ischemic stroke utilizing intact brain slices is demonstrated by a prophylactic treatment of ceria nanoparticles prepared with malic acid.

15 Claims, No Drawings

(56) References Cited

U.S. PATENT DOCUMENTS

| | | |
|---|---|---|
| 6,271,269 B1 | 8/2001 | Chane-Ching et al. |
| 6,305,626 B1 | 10/2001 | Korstvedt |
| 6,362,314 B2 | 3/2002 | Akkara et al. |
| 6,368,366 B1 | 4/2002 | Langer et al. |
| 6,383,237 B1 | 5/2002 | Langer et al. |
| 6,391,995 B2 | 5/2002 | Murugan et al. |
| 6,413,489 B1 | 7/2002 | Ying et al. |
| 6,422,736 B1 | 7/2002 | Antoniades et al. |
| 6,509,319 B1 | 1/2003 | Raad et al. |
| 6,627,720 B2 | 9/2003 | Campbell et al. |
| 6,634,576 B2 | 10/2003 | Verhoff et al. |
| 6,645,262 B1 | 11/2003 | Sanduja et al. |
| 6,649,156 B1 | 11/2003 | Chane-Ching |
| 6,723,138 B2 | 4/2004 | Nickel et al. |
| 6,725,653 B2 | 4/2004 | Brown et al. |
| 6,745,961 B2 | 6/2004 | Korstvedt |
| 6,752,979 B1 | 6/2004 | Talbot et al. |
| 6,869,584 B2 | 3/2005 | Ying et al. |
| 6,892,531 B2 | 5/2005 | Rim |
| 6,897,270 B2 | 5/2005 | Ozawa et al. |
| 6,955,589 B2 | 10/2005 | Kordonski |
| 6,962,681 B2 | 11/2005 | Maganas et al. |
| 7,008,965 B2 | 3/2006 | Chane-Ching |
| 7,025,943 B2 | 4/2006 | Zhou et al. |
| 7,063,729 B2 | 6/2006 | Valentine et al. |
| 7,169,196 B2 | 1/2007 | Wakefield |
| 7,189,768 B2 | 3/2007 | Baran et al. |
| 7,195,653 B2 | 3/2007 | Hazarika et al. |
| 7,384,888 B2 | 6/2008 | Kuno |
| 7,419,516 B1 | 9/2008 | Seal et al. |
| 7,534,453 B1 | 5/2009 | Rzigalinski et al. |
| 7,709,411 B2 | 5/2010 | Zhou et al. |
| 7,803,201 B2 | 9/2010 | Zhou et al. |
| 7,939,040 B2 | 5/2011 | Larcher et al. |
| 8,679,344 B2 | 3/2014 | Allston |
| 8,883,865 B2* | 11/2014 | DiFrancesco ........ B01J 13/0034 423/263 |
| 2002/0095859 A1 | 7/2002 | Hicks et al. |
| 2002/0110519 A1 | 8/2002 | Ying et al. |
| 2002/0177311 A1 | 11/2002 | Schumacher et al. |
| 2003/0148235 A1 | 8/2003 | Valentine et al. |
| 2003/0154646 A1 | 8/2003 | Hazarika et al. |
| 2003/0162843 A1 | 8/2003 | Chane-Ching et al. |
| 2003/0182846 A1 | 10/2003 | Nelson et al. |
| 2003/0182848 A1 | 10/2003 | Collier et al. |
| 2003/0215378 A1 | 11/2003 | Zhou et al. |
| 2003/0221362 A1 | 12/2003 | Collier et al. |
| 2004/0029978 A1 | 2/2004 | Chane-Ching |
| 2004/0035045 A1 | 2/2004 | Caprotti et al. |
| 2004/0137239 A1 | 7/2004 | Klos et al. |
| 2004/0241070 A1 | 12/2004 | Noh et al. |
| 2005/0005506 A1 | 1/2005 | Henley |
| 2005/0031517 A1 | 2/2005 | Chan |
| 2005/0044778 A1 | 3/2005 | Orr |
| 2005/0060929 A1 | 3/2005 | Caprotti et al. |
| 2005/0066571 A1 | 3/2005 | Wakefield |
| 2005/0152832 A1 | 7/2005 | Ying et al. |
| 2005/0165139 A1 | 7/2005 | Kawakami et al. |
| 2005/0227864 A1 | 10/2005 | Sutorik et al. |
| 2006/0000140 A1 | 1/2006 | Caprotti et al. |
| 2006/0005465 A1 | 1/2006 | Blanchard et al. |
| 2006/0027484 A1 | 2/2006 | Leck et al. |
| 2006/0057048 A1 | 3/2006 | Chan et al. |
| 2006/0083694 A1 | 4/2006 | Kodas et al. |
| 2006/0185644 A1 | 8/2006 | Hashimoto et al. |
| 2006/0254130 A1 | 11/2006 | Scattergood |
| 2007/0224092 A1 | 9/2007 | Miyairi et al. |
| 2007/0254994 A1 | 11/2007 | Giannelis |
| 2008/0009410 A1 | 1/2008 | Okamoto et al. |
| 2008/0038552 A1* | 2/2008 | Noack ..................... A61K 8/02 428/402 |
| 2008/0161213 A1 | 7/2008 | Jao et al. |
| 2009/0092671 A1* | 4/2009 | Rzigalinski ............ A61K 33/24 424/489 |
| 2009/0215614 A1 | 8/2009 | Chane-Ching |
| 2010/0088949 A1 | 4/2010 | Reed |
| 2010/0101637 A1* | 4/2010 | Yamasaki ............. B22F 1/0022 136/252 |
| 2010/0135937 A1 | 6/2010 | O'Brien et al. |
| 2010/0152077 A1 | 6/2010 | Allston et al. |
| 2010/0199547 A1 | 8/2010 | Reed |
| 2010/0221344 A1 | 9/2010 | Seal |
| 2010/0242342 A1* | 9/2010 | Reed .................... B01J 13/0034 44/354 |
| 2011/0056123 A1 | 3/2011 | Difrancesco et al. |
| 2013/0273659 A1* | 10/2013 | Costanzo .............. B22F 1/0018 435/455 |

FOREIGN PATENT DOCUMENTS

| | | |
|---|---|---|
| JP | 2002537308 A | 11/2002 |
| JP | 2003520748 A | 7/2003 |
| JP | 2004502022 A | 1/2004 |
| JP | 2004507343 A | 3/2004 |
| JP | 2005508442 A | 3/2005 |
| JP | 2005139029 A | 6/2005 |
| JP | 2006040556 A | 2/2006 |
| JP | 2006506524 A | 2/2006 |
| JP | 2007051057 A | 3/2007 |
| JP | 2007512412 A | 5/2007 |
| JP | 2007283289 A | 11/2007 |
| JP | 2008538349 A | 10/2008 |
| JP | 2008273781 A | 11/2008 |
| WO | 9818884 A2 | 5/1998 |
| WO | 9845212 A1 | 10/1998 |
| WO | 0200812 A2 | 1/2002 |
| WO | 0246336 A2 | 6/2002 |
| WO | 02090260 A1 | 11/2002 |
| WO | 2004065529 A1 | 8/2004 |
| WO | 2004104141 A2 | 12/2004 |
| WO | 2005012465 A1 | 2/2005 |
| WO | 2007002662 | 1/2007 |
| WO | WO 2007/002662 | 11/2007 |
| WO | 2008002323 | 1/2008 |
| WO | 2008030815 | 3/2008 |
| WO | WO 2008/002323 A2 | 4/2008 |
| WO | PCT/US2007/077545 | 1/2009 |
| WO | 2012129279 | 9/2012 |
| WO | 2012129279 A2 | 9/2012 |

OTHER PUBLICATIONS

Robert A. Yokel et al., Biodistribution and oxidative stress effects of a systemically-introduced commercial ceria . . . , Nanotoxicology, 3(3) 234-248 (2009).

T. Masui et al., Synthesis of cerium oxide nanoparticles by hydrothermal crystallization with citric acid, J. Materials Science Letters, 21, 489-491 (2002).

S.S. Hardas et al., Brain Distribution and Toxicological Evaluation of a Systemically Delivered Engineered Nanoscale Ceria, Toxicological Sciences, 116(2), 562-576 (2010).

A.S. Karakoti et al., Direct Synthesis of Nanoceria in Aqueous Polyhydroxyl Solutions, J. Phys. Chem. C 111, 17232-17240 (2007).

A.S. Karakoti et al., Nanoceria as Antioxidant: Synthesis and Biomedical Applications, JOM (J. of the Minerals, Metals & Materials Society), 60(3), 33-37 (2008).

Rzigalinski, B.A., "Nanoparticles and cell longevity," Dec. 2005, pp. 651-659, vol. 4(6), Technology in Cancer Research & Treatment (Abstract only).

Yokel, R.A., et al., "Biodistribution and oxidative stress effects of a systemically-introduced commercial ceria engineered nanomaterial," Sep. 9, 2009, pp. 234-248, vol. 3(3), Nanotoxicology (Abstract only).

Hardas, S.A., et al., "Brain distribution and toxicological evaluation of a systemically delivered engineered nanoscale ceria," May 10, 2010, pp. 562-576, vol. 116(2), Toxicological Sciences.

Karakoti, A.S., et al., "Direct synthesis of nanoceria aqueous polyhydroxyl solutions," Oct. 30, 2007, pp. 17232-17240, vol. 111(46), The Journal of Physical Chemistry C (Abstract only).

(56) References Cited

OTHER PUBLICATIONS

Karakoti, A.S., et al., "Nanoceria as antioxidant: Synthesis and biomedical applications," Mar. 25, 2008, pp. 33-37, vol. 60(3), Journal of the Minerals, Metals & Materials Society (Abstract only).
Estevez, A.Y., et al., "Neuroprotective mechanisms of cerium oxide nanoparticles in a mouse hippocampal brain slice model of ischemia," Sep. 15, 2011, pp. 1155-1163, vol. 51(6), Free Radical Biology and Medicine, (Abstract only).
International Search Report for International Application No. PCT/US2014/061044 dated Jan. 29, 2015, 4 pages.
International Preliminary Report on Patentability and Written Opinion of the International Searching Authority for International Application No. PCT/US2014/061044 dated Apr. 19, 2016, 8 pages.
Masui, T., et al., "Synthesis of cerium oxide nanoparticles by hydrothermal crystallization with citric acid," 2002, pp. 489-491, vol. 21(6), Journal of Materials Science Letters.
Aneggi et al., "Promotional Effect of Rare Earths and Transition Metals in the Combustion of Diesel Soot Over CeO2 and CeO2—ZrO2", Catalysis Today, 114, pp. 40-47 2006.
Australian Patent Examination No. 1 for corresponding Australian Patent Application No. 2011/253488, dated Dec. 2, 2013—3 Pages 2013
Bedrane et al., "Investigation of the Oxygen Storage Process on Ceria- and Ceria-Zirconia-Supported Catalysts", Catalysis Today, 75, pp. 401-405 2002.
Bera et al., "Structural Investigation of Combustion Synthesized CuCeO2 Catalysts by EXAFS and other Physical Techniques: Formation of a Ce1—xCux02—Solid Solution", Chem. Mater., 14, pp. 3591-3601 2002.
Bera at el., "Studies on Cu/CeO2: A New NO Reduction Catalysts", Journal of Catalysts, 186, pp. 36-44 1999.
Born et al., " Reduction of Soot Emission at a DI Diesel Engine by Additional Injection of Hydrogen Peroxide During Combustion", International Fall Fuels and Lubricants Meeting and Exposition, San Francisco, CA, Oct. 19-22, 1998, SAE Technical Paper Series No. 982676, PA, USA 1998.
Canadian Office Action for corresponding Canadian Patent Application No. CA2662765, dated Dec. 17, 2013.
Canadian Office Action for corresponding Canadian Patent Application No. 2662769, dated Jul. 17, 2013.
Canadian Office Action for corresponding Canadian Patent Application No. 2662782, dated Mar. 8, 2013.
Canadian Office Action for corresponding Canadian Patent Application No. 2662782, dated Nov. 25, 2013.
"Cerium: A Guide to its Role in Chemical Technology", cover pg./p. 11, Library of Congress Card No. 92-93444, USA 1992.
Chen et al., "Rare Earth Nanoparticles Prevent Retinol Degeneration Induced by Intracellular Peroxides", Nature Nanotechnology, vol. 1, Nov. 2006, pp. 142-150 2006.
De Guire et al., "Point Defect Analysis and Microstructural Effects in Pure and Donor-Doped Ceria", Solid State Ionics, 52, (1992), pp. 155-163.
Deshpande et al., "Size Dependency Variation in Lattice Parameter and Valency States in Nanocrystalline Cerium Oxide", Applied Physics Letters, 2005, vol. 87, 133113-1, American Institute of Physics, USA—3 Pages.
European Extended (Supplementary) European Search Report issued in EP07814661.0-1270/2074201, PCT US2007/077543, dated Aug. 16, 2011, EPO, The Hague, NL—8 Pages.
European Extended (Supplementary) European Search Report issued in EP07814656-1270/2066767, PCT US2007/077535, dated Nov. 4, 2011, EPO, The Hague, NL—10 Pages.
European Search Report dated Apr. 11, 2013 in corresponding European Application Serial No. 08879024.1—7 Pages.
Evaluation of Human Health Risk from Cerium Added to Diesel Fuel:, HEI Communication 9, Aug. 2001, 64 Pages (entire publication) Health Effects Institute, MA, USA.
Griffith et al., "Correlating Microemulsion Fuel Composition, Structure, and.Combustion Properties", Oak Ridge National Laboratory document TM-11248, Jan. 1, 1989, 45 Pages, Oak Ridge, TN, US.

Indian Office Action for Indian Application No. 1203/KOLNP/2009, dated Jan. 21, 2014—2 Pages.
International Preliminary Examination Report for International Application No. PCT/US2007/077535, dated Oct. 22,2008—8 pages.
"Joint TMC/SAE Fuel Consumption Test-Procedure—Type II", SAE J1321, Oct. 1986, 29 Pages, Society of Automotive Engineers, Inc. USA.
Japanese Office Action for Japanese Application No. 2009-527516, dated Dec. 25, 2012—10 Pages.
Japanese Office Action for Japanese Application No. 2009-527516, dated Jul. 23, 2013—6 Pages.
Japanese Office Action for Japanese Application No. 2011-542092, dated Jul. 24, 2013—7 Pages.
Leubner, I., "Particle Nucleation and growth Models", Current Opinion in Colloid & Interface Science, 2000, vol. 5, Elsevier Science, Ltd. USA, pp. 151-159.
Leubner, I., "A Balanced Nucleation and Growth Model for Controlled Precipitations", J. Dispersion Science and Technology, 2001, vol. 22, No. 1, pp. 125-138.
Leubner, I., "Balanced Nucleation and Growth Model for Controlled Crystal Size Distribution", J. of Dispersion Science and Technology, vol. 23, No. 4, 2002, pp. 577-590.
Mamontov et al., "Lattice Defects and Oxygen Storage Capacity of Nanocrystalline Ceria and Ceria-Zirconia", J. Phys. Chem., B 2000, 104, pp. 11110-11116.
Mexican Office Action (English translation only) for corresponding Mexican Patent Application No. 2011/253488, dated Dec. 2, 2013—2 Pages.
Norris et al., "Doped Nanocrystals", Science, Mar. 28, 2008, vol. 319, pp. 1776-1779, www.sciencemag.org.
Notification of Transmittal of the International Search Report and the Written Opinion of the International Searching Authority (Form PCT/ISA/220), International Search Report (Form PCT/ISA/210) and Written Opinion (Form PCT/ISA/237) issued in the International Application No. PCT/US2011/000858, dated Oct. 24, 2011—1 Page.
Pang et al., "Aluminum Oxide Nanoparticles Prepared by Water-in-Oil Microemulsions", J. Mater. Chem., 2002, vol. 12, pp. 3699-3704, The Royal Society of Chemistry.
Patil et al., "Synthesis of Nanocrystalline Ceria Particles for High Temperature Oxidation Resistant Coating", Journal of Nanoparticles Research, vol. 4, pp. 433-438, 2002.
Perez-Alonso et al., "Synergy of FexCe1—xO2 Mixed Oxides for N2O Decompositions", Journal of Catalysis, vol. 239, pp. 340-346, 2006.
Reddy et al., "Surfactant-Controlled and Microwave-Assisted Synthesis of Highly Active CexZr1—xO2 Nano-Oxides for CO Oxidation".
Ruisheng et al., "Solid Phase Synthesis of Ce—O, Fe—O Catalysts and Their Catalytic Activities in Methane Combustion", Petrochemical Technology, 2006, vol. 35, Issue 4, pp. 319-323.
Sarkas et al., "Nanocrystalline Mixed Metal Oxides—Novel Oxygen Storage Materials", NSTI—Nanotech 2004, vol. 3, pp. 496-498, CRC Press.
Sathamurthy et al., "Reverse Micellar Synthesis of Cerium Oxide Nanoparticles", Nanotechnolgy, 2005, vol. 16, pp. 1960-1964 IOP Publishing, Ltd., UK.
Tarnuzzer et al., "Vacancy engineered Ceria Nanostructures for Protection from Radiation-Induced Damage", Nano Letters, 2005, vol. 5, No. 12, pp. 2573-2577, American Chemical Society , USA.
Terribile et al., "The Preparation of High Surface Area CeO2—ZrO2 Mixed Oxides by a Surfactant-Assisted Approach", Catalysis, 1998, vol. 43, pp. 79-88.
Trovarulli, A., "Catalysis by Ceria and Related Materials", Catalytic Science Series, vol. 2, 2002, Cover page/pp. 37-46, Imperial College Press, London, England 2017.
Tsunekawa et al., "Structural Study on Monosize CeO2-x Nano-Particles", Nanostructural Materials, 1999, vol. 11, No. 1, pp. 141-147, Acta Metallurgica Inc., USA.
Tuller et al., "Doped Ceria as a Solid Oxide Electrolyte", Solid State Science and Technology, Feb. 1975, vol. 122, No. 2, pp. 255-259, Journal of the Electrochemical Society, NY, USA.

(56) References Cited

OTHER PUBLICATIONS

Wang et al., "Unusual Physical and Chemical Properties of Cu in Ce1—xCuxO2 Oxides", J. Phys. Chem. B., 2005, vol. 109, pp. 19595-19603, American Chemical Society, USA.

Wang et al., "Nanoscale Heterogeneity in Ceria Zirconia with Low-Temperature Redox Properties", J. Phys. Chem. B.,46 2006, vol. 110, pp. 18278-18285, American Chemical Society, USA.

Written Opinion of the ISA for PCT/US2007/077535, issued by the ISA/US, dated Jan. 29, 2008—7 Pages.

Written Opinion of the ISA for PCT/US2007/077543, issued by the ISA/US, dated Jan. 29, 2008—5 Pages.

Written Opinion of the ISA for PCT/US2007/077545, issued by the ISA/US, dated Oct. 30, 2008—10 Pages.

Zhang et al., "Preparation of Discrete Nanosize Ceria Powder", Ceramics International, vol. 30, (2004), pp. 997-1002.

"Development of Reference Doses and Reference Concentrations for Lanthanides", Prepared for the Bureau of Land Management National Applied Resource Sciences Center, Nov. 11, 1999, 52 Pages (Entire Publication), Toxicology Excellence for Risk Assesment, USA.

Yang et al., "Effects of Zr Doping on Stoichiometric and Reduced Ceria: A Fist-Principles Study", The Journal of Chemical Physics, 2006, vol. 124 224704, Am erican Institute of Physics, USA—7 Pages. 2006.

Zhang et al., "Cerium OXide Nanoparticles: Size-Selective Formation and Strucuter Analysis", Applied Physics Letters, Jan. 7, 2002, Vo. 80, No. 1, pp. 127-129, American Instiute of Physics, USA 2002.

Zhang et al., "Ceria Nanoparticles: Size, Size Distribution, and Shape", Journal of Applied Physics, Apr. 15, 2004, vol. 95, No. 8, pp. 4319-4326, American Institute of Physics, USA. 2004.

\* cited by examiner

MALIC ACID STABILIZED NANOCERIA PARTICLES

CROSS REFERENCE TO RELATED APPLICATIONS

This patent application is the U.S. national phase filing under 35 U.S.C. § 371 of International Application No. PCT/US2014/061044, filed Oct. 17, 2014, and claims benefit of priority to Provisional Application Ser. No. 61/961,525, ACID STABILIZED NANOCERIA PARTICLES, filed Oct. 17, 2013, the disclosure of which is incorporated herein by reference in its entirety.

FIELD OF THE INVENTION

The present invention relates in general to improvements in the fields of nanoscience and nanomedicine. In particular, the invention relates to methods of preparing nanoparticles, to nanoparticles comprising biocompatible materials, and to the use of such nanoparticles to prevent and to treat disease, more particularly, to reduce complications due to oxidative stress, such as ischemic stroke.

BACKGROUND OF THE INVENTION

The origin of the use of nanoceria in nanomedicine can be traced to the seminal work of Bailey and Rzigalinski, wherein the application of ultrafine cerium oxide particles to brain cells in culture was observed to greatly enhanced cell survivability, as described by Rzigalinski in Nanoparticles and Cell Longevity, *Technology in Cancer Research & Treatment* 4(6), 651-659 (2005). More particularly, rat brain cell cultures in vitro were shown to survive approximately 3-4 times longer when treated with 2-10 nanometer (nm) sized cerium oxide nanoparticles synthesized by a reverse micelle micro emulsion technique, as disclosed by Rzigalinski et al. in U.S. Pat. No. 7,534,453, filed Sep. 4, 2003.

Subsequently, a host of problems with these particular nanoceria particles was disclosed by Rzigalinski et al. in WO 2007/002662. Nanoceria produced by the reverse micelle micro emulsion technique suffered as follows: (1) particle size was not well-controlled within the reported 2-10 nanometer (nm) range, making variability between batches high; (2) tailing of surfactants, such as sodium bis(ethylhexyl)sulphosuccinate, also known as docusate sodium or (AOT), used in the process into the final product caused toxic responses; (3) inability to control the amount of surfactant tailing posed problems with agglomeration when these nanoparticles were placed in biological media, resulting in reduced efficacy and deliverability; and (4) instability of the valence state of cerium (+3/+4) over time. Thus, the cerium oxide nanoparticles produced by the reverse micelle micro emulsion technique were highly variable from batch to batch, and showed higher than desired toxicity to mammalian cells.

As an alternative, Rzigalinski et al. in WO 2007/002662 describe the biological efficacy of nanoceria synthesized by high temperature techniques, obtained from at least three commercial sources. These new sources of cerium oxide nanoparticles were reported to provide superior reproducibility of activity from batch to batch. It was further reported that, regardless of source, cerium oxide particles having a small size, narrow size distribution, and low agglomeration rate are most advantageous. In regard to size, this disclosure specifically teaches that in embodiments where particles are taken into the interior of cells, the preferable size range of particles that are taken into the cell are from about 11 nm to about 50 nm, such as about 20 nm. In embodiments where particles exert their effects on cells from outside the cells, the preferable size range of these extracellular particles is from about 11 nm to about 500 nm.

These inventors (Rzigalinski et al.) also report that for delivery (administration), the nanoparticles were advantageously in a non-agglomerated form. To accomplish this, they reported that stock solutions of about 10% by weight could be sonicated in ultra-high purity water or in normal saline prepared with ultra-high purity water. However, we have confirmed what others have observed, that sonicated aqueous dispersions of nanoceria (synthesized by high temperature techniques and obtained from commercial sources) are highly unstable, and settle rapidly (i.e. within minutes), causing substantial variability in administering aqueous dispersions of nanoceria derived from these sources.

Yokel et al. in *Nanotoxicology*, 2009, 3(3): 234-248, describe an extensive study of the biodistribution and oxidative stress effects of a commercial ceria nanomaterial. In particular, a 5% nanoceria dispersion obtained from Aldrich (#639648) was sonicated for 3 minutes and infused into rats at 50, 250 and 750 mg/kg nanoceria dose. The nature of any nanoparticle surface stabilizer(s) was unknown for this material. The size of the nanoceria particles was characterized by a variety of techniques and reported to be on average 31+/−4 nm by dynamic light scattering. Transmission electron microscopy (TEM) revealed that most of the particles were platelets with a bimodal size distribution with peaks at 8 nm and 24 nm, along with some particles ~100 nm. It was observed that blood incubated for 1 hour with this form of nanoceria had agglomerates ranging from ~200 nm to greater than 1 micron, and that when infused into rats, it was rapidly cleared from the blood (half-life of 7.5 minutes). Most of the nanoceria was observed to accumulate in the liver and spleen, while it was not clear that any substantial amount had penetrated the blood brain barrier and entered brain tissue cells.

This group of authors then sought precise control over the nanoceria surface coating (stabilizer) and prepared stable aqueous dispersions of nanoceria by the direct two-step hydrothermal preparation of Masui et al., *J. Mater. Sci. Lett.* 21, 489-491 (2002), which included sodium citrate as a biocompatible stabilizer. High resolution TEM revealed that this form of nanoceria possessed crystalline polyhedral particle morphology with sharp edges and a narrow size distribution of 4-6 nm. Citrate stabilized dispersions of these 5 nm average ceria nanoparticles were reported to be stable for more than 2 months at a physiological pH of 7.35 and zeta potential of −53 mV. Thus no sonication prior to administration was required.

Results of an extensive biodistribution and toxicology study of this form of citrate stabilized nanoceria was reported by this group of authors in Hardas et al., *Toxicological Sciences* 116(2), 562-576 (2010). Surprisingly, they report that compared with the previously studied ~30 nm nanoceria (Aldrich (#639648) described above), this nanoceria was more toxic, was not seen in the brain, and produced little oxidative stress effect to the hippocampus and cerebellum. The results were contrary to the hypothesis that smaller engineered nanomaterial would readily permeate the blood brain barrier.

While cerium oxide containing nanoparticles can be prepared by a variety of techniques known in the art, the particles typically require a stabilizer to prevent undesirable agglomeration of the nanoparticles. In regard to biocompatible nanoceria stabilizers used previously, once again, Masui et al., *J. Mater. Sci. Lett.* 21, 489-491 (2002) describe a two-step hydrothermal process that directly produces stable aqueous dispersions of ceria nanoparticles that use citrate buffer as a stabilizer. However, this process is both time and equipment intensive, requiring two separate 24 hour reaction steps in closed reactors.

Sandford et al., WO 2008/002323 A2, describe an aqueous preparation technique using biocompatible acetic acid stabilizer that directly produces nanoparticle dispersions of cerium dioxide without precipitation and subsequent calcination. Cerous ion is slowly oxidized to ceric ion by nitrate ion, and a stable non-agglomerated sol of 11 nm crystallite size (and approximately equal grain size) is obtained when acetic acid is used as a stabilizer.

DiFrancesco et al. in commonly assigned PCT/US2007/077545, METHOD OF PREPARING CERIUM DIOXIDE NANOPARTICLES, filed Sep. 4, 2007, describes the oxidation of cerous ion by hydrogen peroxide at low pH (<4.5) in the presence of biocompatible alpha-hydroxy carboxylic acid stabilizers, such as lactic acid, tartaric acid, gluconic acid and 2-hydroxybutanoic acid. Specifically, the stabilizer lactic acid and the stabilizer combination of lactic acid and ethylenediaminetetraacetic acid (EDTA) are shown in working examples to directly produce stable dispersions of nanoceria particles of average particle size in the range of 3-8 nm under highly acidic reaction conditions.

Karakoti et al. in *J. Phys. Chem. C* 111, 17232-17240 (2007) describe the direct synthesis of nanoceria in mono/polysaccharides by oxidation of cerous ion in both acidic conditions (by hydrogen peroxide) and basic conditions (by ammonium hydroxide). The specific biocompatible stabilizers disclosed include glucose and dextran. Individual particle sizes as small as 3-5 nm are disclosed, however, weak agglomerates of 10-30 nm resulted. While the source of the colloidal instability is not described, we speculate that the magnitude of the zeta potential of these particles may not have been sufficiently large.

Karakoti et al. in JOM (Journal of the Minerals, Metals & Materials Society) 60(3), 33-37 (2008) comment on the challenge of synthesizing stable dispersions of nanoceria in biologically relevant media, so as to be compatible with organism physiology, as requiring an understanding of colloidal chemistry (zeta potential, particle size, dispersant, pH of solution, etc.) so as not to interfere with the reduction/oxidation (redox) ability of the nanoceria that enables the scavenging of free radicals (reactive oxygen species (ROS) and reactive nitrogen species). These authors specifically describe the oxidation of cerium nitrate by hydrogen peroxide at low pH (<3.5) in the absence of any stabilizer, as well as, in the presence of dextran, ethylene glycol and polyethylene glycol (PEG) stabilizers. Particle sizes of 3-5 nm are reported, although particle agglomeration to 10-20 nm is also disclosed.

As described above, various methods and apparatus have been reported for preparing dispersions of nanoceria particles. However, a need remains for further improvements in methods for the direct preparation of biocompatible dispersions of nanoceria particles, for example, without isolation and subsequent dispersal of the nanoparticles, and without a calcination step to impart crystallinity, in higher yield, in a shorter period of time and at higher suspension densities, that are sufficiently small in size (e.g. sufficiently small in size to evade detection by an immune system), uniform in size frequency distribution, stable and non-toxic in a wide range of biological media. In addition, it would be desirable to produce dispersions of these nanoparticles that are compatible with physiological pH conditions.

SUMMARY OF THE INVENTION

In accordance with a first aspect the invention, a process of making a dispersion of nanoparticles is provided, comprising: forming a reaction mixture comprising cerous ion, malic acid, an oxidant, and water; optionally, heating or cooling the reaction mixture, and directly forming, without isolation of the nanoparticles, a dispersion of ceria nanoparticles.

In a second aspect of the invention, a nanoparticle comprising ceria and malic acid, is provided.

In a third aspect of the invention, a ceria nanoparticle prepared in the presence of malic acid, is provided.

In a fourth aspect of the invention, a pharmaceutical composition for the prevention and/or treatment of an oxidative stress related event, in particular ischemic stroke, or an oxidative stress related disease, and in particular, a central nervous system disease, such as multiple sclerosis or amyotrophic lateral sclerosis, comprises a ceria nanoparticle prepared in the presence of malic acid, is provided.

In a fifth aspect of the invention, a process of preventing (i.e. prophylactically treating) an oxidative stress related event, in particular ischemic stroke, or an oxidative stress related disease, and in particular, a central nervous system disease, such as multiple sclerosis or amyotrophic lateral sclerosis, comprising administering prior to the onset of the event or disease, an effective amount of a ceria nanoparticle prepared in the presence of malic acid, or, a nanoparticle comprising ceria and malic acid, is provided.

In a sixth aspect of the invention, a process of treating an oxidative stress related event, in particular ischemic stroke, or an oxidative stress related disease, and in particular, a central nervous system disease, such as multiple sclerosis or amyotrophic lateral sclerosis, comprising administering after the onset of the event or disease, an effective amount of a ceria nanoparticle prepared in the presence of malic acid, or, a nanoparticle comprising ceria and malic acid, is provided.

DETAILED DESCRIPTION OF THE INVENTION

It is to be understood that elements not specifically shown or described may take various forms well known to those skilled in the art. The invention is defined by the claims.

In this disclosure, the term nanoparticle includes particles having a mean diameter of less than 100 nm. For the purposes of this disclosure, unless otherwise stated, the diameter of a nanoparticle refers to its average crystallographic particle diameter, which can be estimated by a peak width analysis of powder X-ray diffraction (XRD) spectra using the Scherrer equation. Alternatively, the geometric particle diameter can be estimated by analysis of transmission electron micrographs (TEM). Alternatively, the hydrodynamic diameter, which includes molecular adsorbates and the accompanying solvation shell of the particle, can be determined by dynamic light scattering techniques. In addition, for substantially monodisperse nanoparticle size distributions having geometric size in the 1-10 nm range, XRD can also reveal a very low angle scattering peak that is a direct measure of the size of the scattering centers.

In this disclosure, malic acid refers to 2-hydroxybutanedioic acid (CAS No. 6915-15-7), an alpha-hydroxy dicarboxylic acid of molecular formula $C_4H_6O_5$ and chemical structural formula $HO_2CCH_2CH(OH)CO_2H$, and to salts thereof.

In this disclosure, the term "isolation" is understood to encompass any conventional solid/liquid separation technique, such as, for example, filtration, settling, draining, evaporation, drying or centrifugation.

In this disclosure, the term "metal" in referring to elements of the Periodic Table includes all elements other than those of the following atomic numbers: 1-2, 5-10, 14-18, 33-36, 52-54, 85 and 86.

The term "transition metal" is understood to encompass the 30 chemical elements of atomic number 21 to 30, 39 to 48, 57, and 72 to 80, which are included in Periods 4, 5, 6, respectively, of the Periodic Table.

The term "rare earth metal" is understood to encompass the 14 lanthanide chemical elements of atomic number 58 to 71, and the 14 actinide chemical elements of atomic number 90 to 103.

The term "alkali metal" is understood to encompass the 6 chemical elements forming Group 1 of the Periodic Table, those of atomic number 3, 11, 19, 37, 55, and 87.

The term "alkaline earth metal" is understood to encompass the 6 chemical elements forming Group 2 of the Periodic Table, those of atomic number 4, 12, 20, 38, 56, and 88.

In this application, the term "crystalline" is understood to describe a material that displays at least one X-ray or electron diffraction peak (excluding very low angle XRD peaks not assignable to a crystal structure), wherein the peak intensity is discernibly greater than the background scattering (baseline noise). The terms "semi-crystalline" or "partially crystalline" are understood to describe a material that displays only broad X-ray or electron diffraction peaks of low peak intensity due to a lack of long-range order. The term "amorphous" is understood to describe a material that does not display any X-ray or electron diffraction peaks (excluding very low angle XRD peaks not assignable to a crystal structure).

In this application, various cerium-containing materials are nominally described as a "ceria" phase, "cerium oxide" phase or "cerium dioxide" phase. It will be understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for bulk oxide phases comprised of metal cations of multiple oxidation states, it is understood that the total amount of oxidic anions present will be determined by the specific amounts of the various oxidation states of the metal cations present, for example, cerous ion ($Ce^{3+}$) and ceric ion ($Ce^{4+}$), such that charge neutrality is maintained. For non-stoichiometric phases nominally described as metal dioxides, this is embodied in the chemical formula $MO_{2-\delta}$, wherein the value of δ (delta) may vary.

For a cerium oxide, $CeO_{2-\delta}$, the value of δ (delta) typically ranges from 0.0 to 0.5, the former denoting cerium (IV) oxide, $CeO_2$, the latter denoting cerium (III) oxide, $CeO_{1.5}$ (alternatively denoted $Ce_2O_3$). While not wishing to be held to any particular theory, the value of δ (delta) may be interpreted as the amount of oxygen vacancies present relative to cerium (IV) oxide ($CeO_2$). For each oxygen di-anion vacancy present, two cerous ions ($Ce^{3+}$) are present, to preserve charge neutrality.

In this application, the term "cerium dioxide" is understood to describe Cerium (IV) oxide ($CeO_2$).

In this application, the term "ceria" is understood to describe a cerium oxide comprising ceric ion (i.e. $Ce^{4+}$ or cerium (IV) ion), encompassing a range of non-stoichiometric materials described by the chemical formula, $CeO_{2-\delta}$, wherein the value of δ (delta) ranges from 0.0 to less than 0.5.

In this application, the terms "nanoceria particles", "ceria nanoparticles" and "cerium oxide nanoparticles" have the same meaning and are used interchangeably.

In accordance with one aspect of the invention, a process is provided comprising: forming a reaction mixture comprising cerous ion, malic acid, an oxidant, and water; and thereafter forming a dispersion of nanoparticles in the reaction mixture.

In a particular embodiment, the dispersion of nanoparticles is formed directly in the reaction mixture, without isolation of the nanoparticles.

In particular embodiments, the reaction mixture is heated or cooled to a temperature in the range of about 0° C. to about 100° C. In particular embodiments, the reaction mixture is heated or cooled to temperatures greater than 20° C., or less than or equal to 20° C. In various embodiments, the reaction mixture is heated or cooled to temperatures greater than about 30° C., about 40° C., about 50° C., about 60° C., about 70° C., about 80° C. or about 90° C.

In embodiments employing elevated reaction temperatures, the duration of time at elevated temperature may vary widely, for example, from minutes to hours. In various embodiments, a reaction temperature in the range of about 40° C. to about 95° C. is maintained for a time ranging from about 10 minutes to about 4 hours.

In particular embodiments, the nanoparticles formed are dehydrated, dehydroxylated or deprotonated by heating of the reaction mixture.

In a particular embodiment, the crystallinity of the nanoparticles formed is enhanced by heating of the reaction mixture.

In various embodiments, the reaction mixture or nanoparticles formed comprise a minor amount of a metal ion other than a cerium ion, such as, for example, a transition metal ion, rare earth metal ion other than cerium, alkaline earth metal ion or an alkali metal ion. In particular embodiments, the metal ion other than a cerium ion is an iron ion, such as a ferrous ion or a ferric ion. In other particular embodiments, the metal ion other than a cerium ion is a zirconium, platinum, palladium, nickel, copper, lanthanum or yttrium ion.

In various embodiments, the oxidant includes molecular oxygen, present, for example, in air, or compounds more oxidizing than molecular oxygen (or an ambient atmosphere of air). In other embodiments, the oxidant has an aqueous half-cell reduction potential greater than −0.13 volts relative to the standard hydrogen electrode. In particular embodiments the oxidant is an alkali metal or ammonium perchlorate, chlorate, hypochlorite or persulfate; ozone, a peroxide, such as hydrogen peroxide ($H_2O_2$) or tert-butyl hyperoxide; or a combination thereof.

In various embodiments, the amount of oxidant employed varies widely in relation to the total amount of oxidizable metal ions present. In particular embodiments the molar amount of oxidant present is equal to or greater than the total molar amount of oxidizable metal ions. In specific embodiments, two-electron oxidants, such as hydrogen peroxide, are present in at least one-half the molar concentration of total oxidizable metal ions, such as cerous ion or ferrous ion.

In various embodiments, the oxidant is added to the reaction mixture alone or concurrently with one or more of the other reactants.

In a particular embodiment, molecular oxygen is passed through the reaction mixture.

In various embodiments, the pH of the reaction mixture is adjusted by the addition of an acid or base to a value greater than 4.5, greater than 5.0, greater 6.0, greater than 6.5, greater than 7.0 (alkaline conditions), greater than 7.1, greater than 8.0, greater than 9.0, greater than 10.0, or greater than 11.0.

In various embodiments, a dispersion of the nanoparticles is used to treat biological tissues or biological media, and is adjusted to a pH within suitable physiological conditions. In various embodiments, suitable physiological pH conditions range from about 6.5 to about 8.0, or from about 7.0 to about 7.6, or from about 7.1 to about 7.5.

In particular embodiments, the reaction mixture is adjusted to a pH within suitable physiological conditions. In other embodiments, the final product dispersion of ceria nanoparticles is adjusted to a pH within a suitable physiological condition.

In various embodiments, the reaction mixture is formed in a batch reactor, a continuous reactor or a colloid mill. In particular embodiments of a continuous reactor, a continuous-stirred-tank reactor or a plug-flow reactor are used.

The particular embodiments, various mixing devices known in the art are employed to stir, mix, shear or agitate the contents of the reaction mixture. In various embodiments, mixers comprising stir bars, marine blade propellers, pitch blade turbines or flat blade turbines are used. In particular embodiments, a colloid mill or a Silverson® High Shear Mixer is employed. In a particular embodiment, a high shear mixer that forces the reaction mixture to pass through a screen, wherein holes vary in size from fractions of a millimeter to several millimeters, is employed. In particular embodiments, one or more of the reactants is introduced below the surface of the aqueous reaction mixture. In a particular embodiment, a reactant is introduced below the surface of the aqueous reaction mixture in close proximity to a mixing device.

In various embodiments, the nanoparticles formed are amorphous, semi-crystalline or crystalline. Crystalline nanoparticles may be alternatively described as single particle crystallites or as individual crystallites. In particular embodiments, the nanoparticles formed are characterized by a cerium oxide crystal structure. In a particular embodiment the nanoparticles formed are characterized by a cubic fluorite crystal structure.

In various embodiments, the nanoparticles formed have a hydrodynamic diameter less than 100 nm, less than 80 nm, less than 60 nm, less than 40 nm, less than 20 nm, less than 10 nm, less than 5.0 nm or less than about 2.0 nm.

In a particular embodiment of the invention, a nanoparticle comprising cerium and malic acid is provided.

In a particular embodiment, a nanoparticle comprising eerie ion and malic acid is provided.

In a particular embodiment, a nanoparticle comprising ceria and malic acid is provided.

In a particular embodiment, a nanoparticle comprising malic acid and a cerium oxide, cerium hydroxide or cerium oxyhydroxide, is provided.

In various embodiments, the zeta potential of a dispersion of the nanoparticles is altered by adjusting the pH, the malic acid content, or a combination thereof.

In a particular embodiment, the nanoparticle dispersion formed is washed to remove excess ions or by-product salts. In various embodiments, the nanoparticle dispersion is washed such that the ionic conductivity is reduced to less than about 15 millisiemens per centimeter (mS/cm), less than about 10 mS/cm, less than about 5 mS/cm or less than about 3 mS/cm. In particular embodiments, the nanoparticle dispersion formed is washed without isolation of the nanoparticles, such as, for example, by dialysis or diafiltration, thereby maintaining a stable nanoparticle dispersion. In a particular embodiment, the nanoparticle dispersion formed is washed with an aqueous solution containing malic acid.

In particular embodiments, the product nanoparticle dispersions are subsequently concentrated to remove excess solvent or excess water. In particular embodiments, the product nanoparticle dispersion is subsequently concentrated by diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In particular embodiments, the size distribution of the nanoparticles is substantially monomodal. In various embodiments, the nanoparticle size distribution has a coefficient of variation (COV) less than about 30%, less than about 25%, less than about 20%, less than about 15%, less than about 10% or less than about 5%, where the COV is defined as the standard deviation divided by the mean.

In one embodiment of the invention, a process of solvent shifting the aqueous nanoparticle dispersion to a less polar solvent composition by methods disclosed in commonly assigned U.S. Pat. No. 8,679,344, the disclosure of which is hereby incorporated by reference, is employed. In a specific embodiment, the nanoparticle dispersion is passed through a diafiltration column along with the addition of an organic diluent. In a specific embodiment, the organic diluent comprises a surfactant, such as, for example, one or more alcohols or glycol ethers.

Without being bound by any theory, the proposed use of nanoceria for the prevention and/or treatment of inflammation and/or oxidative stress related events and diseases (e.g. reactive oxygen species (ROS) mediated diseases) is based in part upon a belief that cerium oxides may function as catalytic scavengers of free radicals. The existence of and facile inter-conversion of cerium in a mixture of $Ce^{3+}$ and $Ce^{4+}$ valence states may enable cerium oxides to reduce and/or oxidize free radicals to less harmful species in a catalytic or auto-regenerative (cycling) manner. Redox reactions may occur on the surface of cerium oxide nanoparticles that neutralize tissue-damaging free radicals. For example, it is believed to be desirable to oxidize superoxide anion ($O_2^-$) to molecular oxygen, to oxidize peroxynitrite anion ($ONOO^-$) to physiologically benign species, and to reduce hydroxyl radical (.OH) to hydroxide anion. This catalytic behavior may in turn enable a greatly reduced dosing regimen in comparison to, for example, sacrificial antioxidants currently available to treat oxidative stress related diseases and events.

In particular embodiments, administered nanoceria particles are taken into cells through cell membranes and reside in the cellular cytoplasm or in various cellular organelles, such as mitochondria and the nucleus. In other embodiments, the nanoceria particles reside in intravascular or interstitial spaces, wherein they may reduce oxidative stress and inflammation by eliminating free radicals or reducing autoimmune responses. In a particular embodiment, the immune system invasion of the central nervous system resulting from breakdown of the blood-brain barrier (BBB) or blood-cerebrospinal fluid barrier (BCFB) or blood-ocular barrier (BOB) is modulated by nanoceria particles.

In another embodiment, the nanoceria particles are particles capable of crossing a mammalian blood brain barrier.

In various embodiments, nanoceria particles cross a mammalian blood brain barrier and reside in brain parenchyma tissues as aggregates or agglomerates of a size less than about 100 nm, less than about 50 nm, less than about 20 nm, less than about 10 nm, less than about 5 nm. In a particular embodiment, nanoceria particles cross a mammalian blood brain barrier and reside in brain parenchyma tissues as independent, non-agglomerated nanoparticles of a size less than about 3 nm.

In particular embodiments, a pharmaceutical composition comprises nanoparticles comprising ceria and malic acid, or, ceria nanoparticles prepared in the presence of malic acid.

In various embodiments, a pharmaceutical composition comprising nanoparticles comprising ceria and malic acid, or, nanoceria particles prepared in the presence of malic acid, is administered to a human or a non-human subject, such as another mammal, including, but not limited to, a canine, a feline, a bovine, an equine, an ovine, a porcine or a rodent. Alternatively, the subject of administration can be an animal such as a bird, insect, reptile, amphibian, or any companion or agricultural animal. Alternatively, the subject of administration can be a bacterium, yeast, mold, fungus or another single celled organism. The subject of administration may also be a plant.

In another particular embodiment, a process of preventing (i.e. prophylactically treating) an oxidative stress related event, disease or cellular pathology, comprises administering prior to the onset of an event, disease or cellular pathology, an effective amount of a ceria nanoparticle prepared in the presence of malic acid, or, a nanoparticle comprising ceria and malic acid.

In another particular embodiment, a process of treating an oxidative stress related event, disease or cellular pathology, comprises administering after the onset of an event, disease or cellular pathology, an effective amount of a ceria nanoparticle prepared in the presence of malic acid, or, a nanoparticle comprising ceria and malic acid.

In various embodiments, a nanoceria particle of the invention is administered in vivo to a subject by topical, enteral or parenteral methods, including injections, infusions or implantations. More particularly, it is specifically contemplated to administer nanoceria particles of the invention by any of the following routes: auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intraabdominal, intra-amniotic, intra-arterial, intrabiliary, intrabronchial, intrabursal, intracardiac, intracartilaginous, intracaudal, intracavernous, intracavitary, intracerebral, intracisternal, intracorneal, intracornal-dental, intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmammary, transmucosal, transplacenta, transtracheal, transtympanic, ureteral, urethral, vaginal, and any other or unassigned route.

In various embodiments, oxidative stress related events and/or diseases specifically contemplated for prevention and/or treatment include, but are not limited to, Alzheimer's Disease, Parkinson's Disease, Huntington's Disease, amyotrophic lateral sclerosis (ALS), ataxia, Friedreich's ataxia, autism, obsessive-compulsive disorder, attention deficit hyperactivity disorder, migraine, ischemic stroke, traumatic brain injury, cancer, inflammation, autoimmune disorders, lupus, MS, inflammatory bowel disease, Crohn's Disease, ulcerative colitis, stenosis, restenosis, atherosclerosis, metabolic syndrome, endothelial dysfunction, vasospasms, diabetes, aging, chronic fatigue, coronary heart disease, cardiac fibrosis, myocardial infarction, hypertension, angina, Prizmetal's angina, ischemia, angioplasty, hypoxia, Keshan disease, glucose-6-phosphate dehydrogenase deficiency, favism, ischemic reperfusion injury, rheumatoid and osteoarthritis, asthma, chronic obstructive pulmonary disease (e.g. emphysema and bronchitis), allergies, acute respiratory distress syndrome, chronic kidney disease, renal graft, nephritis, ionizing radiation damage, sunburn, dermatitis, melanoma, psoriasis, macular degeneration, retinal degeneration, and cataractogenesis.

In various embodiments, oxidative stress related cellular pathologies specifically contemplated for prevention and/or treatment include, but are not limited to, mitochondrial dysfunction, lysosome and proteasome dysfunction, oxidation of nucleic acids (e.g. RNA and DNA), tyrosine nitration, loss of phosphorylation mediated signaling cascades, initiation of apoptosis, lipid peroxidation and destruction of membrane lipid environments.

In other embodiments, nanoceria particles of the invention are retained in or on the surface of a medical device or prosthesis, such as a cannula, catheter or stent, thereby, for example, reducing inflammation locally or systemically, over either a short or long period of time.

In various embodiments, the nanoceria particles of the invention are delivered in any suitable form known in the art, including, but not limited to, a suspension, gel, tablet, enteric coated tablet, loaded liposome, powder, suppository, infusible, lozenge, cream, lotion, salve, or inhalant.

In various embodiments, the nanoceria particles of the invention are combined with other pharmaceutically acceptable substances, such as, but not limited to, water, salts, buffers, phosphate buffered saline (PBS), sugars, human or bovine serum albumen, lipids, drugs, colorants, flavorants, binders, gums, surfactants, fillers or any excipients known in the art.

In a particular embodiment, the vehicle comprising the nanoceria particles of the invention is sterilized prior to administration.

In other embodiments, a cell or cell culture is contacted with a nanoceria particle or particles of the invention. Contact may be practiced by exposing a cell or cell culture by in vitro or ex vivo methods, wherein the latter method comprises re-introducing the treated cell or cells into a subject, such as the subject from which the cell or cells were originally obtained. In various embodiments the cell is prokaryotic or eukaryotic in nature. In particular embodiments, the treated cells are used in the production of proteins used in the pharmaceutical industry, generally known as biologics, such as, but not limited to, antigens, antibodies and vaccines. In another embodiment, the treated cells are used in a fermentation process.

In an alternative end-use application, nanoceria particles of the invention are employed as a component of a chemicalmechanical polishing reagent for polishing substrates used, for example, in semiconductor devices, ceramics and optical elements. In particular embodiments, nanoceria particles of the invention are admixed into a magnetic fluid that changes in viscosity or other fluid properties upon application of a magnetic field. Some typical end uses for these magnetic fluids include shock absorbers, clutches, heat transfer devices and actuating modules, as described, for example, in U.S. Pat. No. 5,525,249. In a particular embodiment, it is specifically contemplated to employ nanoceria particles of the invention as an abrasive in a magnetorheological finishing (MRF) fluid used, for example, in a lens polishing operation, as described in U.S. Pat. No. 6,955,589. In a particular embodiment, dispersions containing about 20% by weight of the nanoceria particles of the invention are admixed into a MRF fluid. Some goals of adding an ultrafine abrasive such as the nanoceria of the invention to a MRF fluid are increased material removal rate, increased surface smoothness with fewer accompanying physical defects, improved chemical stability (e.g. reduced oxidation of magnetic particles comprising the magnetic fluid) and improved physical stability (e.g. reduced settling) of the MRF fluid.

In another end-use application, nanoceria particles of the invention are used as an inorganic metal oxide core in the preparation of a nanoscale ionic material (NIM) composition, as described, for example, by E. P. Giannelis and A. B. Bourlinos in US 2007/0254994 and by N. Fernandes and E. P. Giannelis in WO 2012129279. A nanoscale ionic material (NIM) composition comprises an inorganic metal oxide core and an organic polymer material canopy. In a particular embodiment, NIM compositions spontaneously form nanoscale ionic liquid (NIL) material compositions that are characterized by transport properties remarkably similar to those of simple molecular liquids, but with negligible vapor pressures. In other embodiments, NIM compositions spontaneously form nanoscale ionic solid (NIS) material compositions and nanoscale ionic gel (NIG) material compositions, the latter containing an intermediate amount of inorganic material content and organic material content, and characterized by physical and chemical properties intermediate to those of NIS material compositions and NIL material compositions.

In a particular embodiment of the invention, a conjugate comprising (1) a nanoparticle comprising ceria and malic acid, or, a ceria nanoparticle prepared in the presence of malic acid; and (2) a biologically active agent, is provided. In particular embodiments, the biologically active agent comprises nucleic acid material, such as, for example, plasmid deoxyribonucleic acid, small interfering ribonucleic acid (siRNA), micro ribonucleic acid (miRNA), or an aptamer/riboswitch. In a particular embodiment the conjugate described supra is used as a cell transfection agent.

The invention is further illustrated by the following examples, which are not intended to limit the invention in any manner.

EXPERIMENTAL SECTION

Nanoparticle Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent.

Quantitative assessments of the particle size of the nanoparticle dispersions can be made by a number of techniques. Particle size estimation by peak-width analysis of X-ray diffraction (XRD) spectra was done using the Scherrer method. Sample preparation for the XRD measurements was done as follows: liquid samples were mixed lightly, placed in a Telfon boat, allowed to dry under a heat lamp for several hours (until nearly dry), the resulting concentrated liquid was then placed onto a zero background quartz disk, allowed to dry under the heat lamp, and then dried in an oven at either room temperature or at about 80° C. for four hours under a dry nitrogen atmosphere. The coated disk was then analyzed by XRD using a nitrogen gas dry cell attachment. The XRD spectra were recorded on a Rigaku D2000 diffractometer equipped with copper rotating anode, diffraction beam graphite monochrometer tuned to copper K-alpha radiation, and a scintillation detector.

Alternatively, dynamic light scattering (DLS) measurements were obtained using a Brookhaven 90Plus Particle Size Analyzer (Brookhaven Instruments Corp., Holtzville, N.Y., U.S.A.) equipped with a quartz cuvette. Samples were typically filtered through a 0.2 micron syringe filter prior to measurement to remove any bacterial contaminants. Reported DLS sizes are the lognormal number weighted parameter. These hydrodynamic particle sizes are typically larger than sizes yielded by other techniques because the DLS technique includes contributions from adsorbed ions or molecules that constitute the solvation sphere of the particle.

Alternatively, the size of the nanoparticles could be determined by direct analysis of transmission electron microscopy (TEM) images of the particles.

Evaluation of Nanoceria Particles in Treating Ischemic Stroke

Mouse Hippocampal Brain Slice Model of Ischemic Stroke:

The ability of nanoceria to reduce oxidative stress was evaluated in a modification of the in vitro mouse hippocampal brain slice model of ischemia described by Estevez, A Y; et al., Neuroprotective mechanisms of cerium oxide nanoparticles in a mouse hippocampal brain slice model of ischemia, *Free Radic. Biol. Med.* (2011)51(6):1155-63 (doi: 10.1016/j.radbiomed.2011.06.006).

Adult (2-5 months of age) CD1 mice were sacrificed via rapid decapitation and their brains quickly removed and placed in a chilled choline-based slicing solution containing 24 mM choline bicarbonate, 135 mM choline chloride, 1 mM kynurenic acid, 0.5 mM $CaCl_2$, 1.4 mM $Na_2PO_4$, 10 mM glucose, 1 mM KCl, and 20 mM $MgCl_2$ (315 mOsm). Transverse hippocampal slices, 400 μm thick, were cut along a rostral-to-caudal axis (−1.2 to −2.8 mm Bregma) using a Leica VT1200 Vibratome (Leica Microsystems, Wetzlar, Germany) and allowed to recover for 1 hr in a control artificial cerebral spinal fluid (aCSF) containing 124 mM NaCl, 3 mM KCl, 2.4 mM $CaCl_2$, 1.3 mM $MgSO_4$, 1.24 mM $K_3PO_4$, 26 mM $NaHCO_3$, 10 mM glucose and bubbled with 5% $CO_2$, 95% $O_2$ gas (pH 7.4, 300 mOsm). Hippocampal slices were placed in a culture dish and stored in a NuAire humidified incubator (NuAire, Plymouth, Minn., USA) at 37° C. with 5% $CO_2$ for up to 48 hr.

Oxidative stress from ischemia was induced by placing the brain slices in hypoglycemic, acidic and hypoxic aCSF (glucose and pH were lowered to 2 mM and 6.8, respectively, and the solution was bubbled with 84% $N_2$, 15% $CO_2$, and 1% $O_2$) at 37° C. for 30 min. Sucrose was added to maintain the osmolarity of the solution at about 295 mOsm.

Aqueous dispersions of cerium oxide nanoparticles prepared as described supra were administered in matched doseage in a delivery volume of 1 μg per 1 ml aCSF or medium (equivalent to 5.8 µM) at the onset of the ischemic event, and remained in the medium throughout the remainder of the experiment. Control slices received an equal volume of vehicle control. Various delivery vehicles were used with similar success for the cerium oxide nanoparticles prepared as described herein, including distilled water alone, saline solution, Na-citrate solution, PBS, and combinations thereof.

After exposure to 30 minutes of oxidative stress (ischemic conditions), the living brain slices (test and control) were incubated for 24 hr in organotypic culture by placing them in a 35 mm culture dish containing culture medium and Millipore inserts (Millipore, Billerica, Mass., USA). Culture medium contained 50% minimum essential medium (Hyclone Scientific, Logan Utah, USA), 25% horse serum, 25% Hank's balanced salt solution (supplemented with 28 mM glucose, 20 mM HEPES and 4 mM $NaHCO_3$), 50 U/ml penicillin, and 50 µl/ml streptomycin, pH 7.2.

The extent of cell death was measured 24 hours after the oxidative injury using fluorescence imaging techniques. Each set of brain slices studied in the test condition (i.e. administered with cerium oxide nanoparticles) was matched with a similar set of control brain slices treated identically in every way except for administration of vehicle alone. Thus on each study day, two sets of anatomically matched brain slices taken from age-matched and sex-matched littermates were subjected to either the test condition (administered with cerium oxide nanoparticles) or control (vehicle alone). During fluorescence imaging measurements, the light intensity, duration of image capture, and timing of image collection were identical for the test condition and vehicle control brain slices. Results were expressed as the ratio of the fluorescence in the test condition to the fluorescence in the matched control slice imaged at the same time point in the experimental sequence.

At 24 hours post oxidative injury, paired (control and test) brain slices were incubated for 20 min in culture medium containing 0.81 µM vital exclusion dye SYTOX® Green (Invitrogen, Carlbad, Calif., USA) and, subsequently, washed for 15-20 min in culture medium to remove unincorporated dye. SYTOX® Green is a fluorescent dye that binds to DNA and RNA. However, it is excluded from the cell nucleus by the cell membrane in intact, viable cells. Therefore, it acts as a vital dye and stains only those dead and dying cells in which the cell membrane has become permeable so that the dye has access to the cell interior. After staining and washing, brain slices were transferred to the stage of a Nikon TE 2000-U (Nikon Instruments, Melville, N.Y., USA) microscope equipped with epifluoresence attachments and a 150-W xenon light source (Optiquip, Highland Mills, N.Y., USA). Control aCSF solution was loaded into 60-ml syringes, equilibrated with 95% $O_2$/5% $CO_2$, and heated to 37° C. using a servo-controlled syringe heater block, stage heater, and in-line perfusion heater (Warner Instruments, Hamden, Conn., USA). The brain sections were continuously perfused with warmed, 95% $O_2$/5% $CO_2$ equilibrated aCSF at a rate of 1 ml per minute. After 5 min, images of the hippocampal formation of each control and test brain slice were collected using a 4× Plan Flour objective (Nikon Instruments) under identical conditions (i.e. light intensity, exposure time, camera acquisition parameters). SYTOX® Green fluorescence was measured by briefly (620 ms) exciting the tissue at 480±40 nm, filtering the emitted fluorescence (535±50 nm) from the probe using a 505 nm, long-pass, dichroic mirror (Chroma technology, Bennington, Vt., USA), intensifying, and measuring with a cooled CCD gain EM camera (Hamamatsu CCD EM C9100; Bridgewater, N.J., USA). The digital images were acquired and processed with Compix SimplePCI 6.5 software (C Imaging Systems, Cranberry Township, Pa., USA).

The light intensity resulting from the SYTOX® Green loading reflected the number of dead or dying cells within the calculated area. The light-intensity measurements were performed automatically using the Compix SimplePCI 6.5 software, thereby eliminating experimenter bias in selecting the regions of interest.

Reduction in cell death is reported as the ratio of the light intensity of SYTOX® Green fluorescence from the cornu ammonis fields (oriens layer, stratum radiatum and lacunosum moleculare) for the test condition (i.e. nanoceria treated) to the control (untreated) for anatomically matched hippocampal sections taken from age-matched and sex-matched littermate brains sliced and exposed to ischemic oxidative stress on the same day, and fluorescence imaged 24 hr after the ischemic insult.

Nanoceria particles were evaluated in the Mouse Hippocampal Brain Slice Model of Ischemic Stroke using a treatment concentration of 5.8 µM. Results for a reduction in cell death, commonly referred to as sparing, are reported as the percent reduction relative to the control (i.e. a positive percentage indicates a reduction in cell death, a negative percentage indicates an increase in cell death).

Example 1

Preparation of Nanoceria with Malic Acid
(Inventive)

DS-145-2

To a 0.6 L beaker at room temperature, 300 grams distilled water, 10 grams cerium(III) nitrate hexahydrate and 5 grams malic acid were added and mixed. After the cerium(III) nitrate and malic acid were dissolved, concentrated ammonium hydroxide (28-30%) was added until the solution pH was 7.6. The solution was yellow in color and clear in appearance. Subsequently, 1.6 grams of hydrogen peroxide (50%) was added. The solution turned orange in color and remained clear. After 5 minutes of stirring, concentrated ammonium hydroxide was added until the pH was 9.5. The solution remained orange, but turned cloudy. The temperature was raised to 70° C. over 30 minutes and held at that temperature for 90 minutes, during which the orange solution lightened in color and became clear. The solution was cooled to room temperature in 60 minutes, and then washed to remove excess salts with distilled water that was pH adjusted to 7.5 with sodium hydroxide, until an ionic conductivity of less than 4 mS/cm was achieved. The pH of the final reaction product was 7.2.

The final reaction product was a clear light orange colored liquid that is typical of dispersions that display a high degree of Tyndall scattering when illuminated with a low intensity LASER beam, a test for well-dispersed colloidal particles. Particle size analysis by dynamic light scattering indicated a hydrodynamic diameter of 2.2 nm with a polydispersity of 0.191. The final reaction product dispersion was observed to be stable (i.e. well-dispersed) for several months. Phase identification by powder XRD analysis indicated the presence of a crystalline cubic fluorite phase iso-structural with $CeO_2$ (PDF #34-394). The average crystallite size for the nanoceria particles was determined to be 1.8 nanometers from analysis of the (220) powder XRD peak width using the Scherrer method.

The aqueous dispersion of nanoceria particles prepared with malic acid as described above was evaluated in the Mouse Hippocampal Brain Slice Model of Ischemic Stroke using a treatment concentration of 5.8 µM ceria. A reduction in cell death of 9% was observed for the aqueous dispersion of nanoceria particles prepared with malic acid relative to a non-ceria containing control, based on a comparison of 17 pairs of anatomically matched brain slices ($\rho=0.057$).

Example 2

Preparation of Nanoceria with Lactic Acid
(Comparative)

WC-46

Aqueous alkaline reaction procedures similar to those used in Example 1 were repeated, except that lactic acid was used instead of malic acid. The final reaction product was an unstable dispersion that resulted in formation of white sediment.

Example 3

Preparation of Nanoceria with Tartaric Acid
(Comparative)

DS-146-2

Aqueous alkaline reaction procedures similar to those used in Example 1 were repeated, except that tartaric acid was used instead of malic acid. The final reaction product was a clear light orange colored liquid that is typical of dispersions that display a high degree of Tyndall scattering when illuminated with a low intensity LASER beam, a test for well-dispersed colloidal particles. Particle size analysis by dynamic light scattering indicated a hydrodynamic diameter of 5.0 nm with a polydispersity of 0.248. However, the final reaction product formed an unstable dispersion that resulted in a cloudy suspension when diluted to the treatment concentration and physiological pH used in the Mouse Hippocampal Brain Slice Model of Ischemic Stroke.

Comparison of the results among Examples 1-3 indicates that among the three alpha-hydroxy carboxylic acids employed as stabilizers only malic acid was effective in forming a stable aqueous dispersion of ceria nanoparticle under alkaline reaction conditions that also remained stable at the treatment concentration and physiological pH conditions used in the Mouse Hippocampal Brain Slice Model of Ischemic Stroke.

The utility of ceria nanoparticles prepared with malic acid to prevent cell death in a model of ischemic stroke utilizing intact murine brain slices was demonstrated in Example 1.

While the invention has been described by reference to various specific embodiments, it should be understood that numerous changes may be made within the spirit and scope of the inventive concepts described. Accordingly, it is intended that the invention not be limited to the described embodiments, but will have full scope defined by claims language.

What is claimed:
1. A process of making nanoparticles, comprising:
   (a) forming a reaction mixture comprising a cerium ion, malic acid, an oxidant, and water; and
   (b) forming in the reaction mixture a dispersion of nanoparticles.
2. The process according to claim 1, wherein said dispersion of nanoparticles is formed directly in the reaction mixture without isolation of the nanoparticles.
3. The process according to claim 1, further comprising the step of adjusting the pH of said reaction mixture to an alkaline condition.
4. The process according to claim 1, further comprising the step of heating or cooling said reaction mixture to a temperature in the range of about 0° C. to about 100° C.
5. The process according to claim 1, wherein said cerium ion comprises cerous ion.
6. The process according to claim 1, wherein said oxidant is hydrogen peroxide.
7. The process according to claim 1, wherein said nanoparticles comprise a cerium oxide phase.
8. The process according to claim 6, wherein said cerium oxide phase has a cubic fluorite structure.
9. The process according to claim 1, wherein said nanoparticles are characterized by a hydrodynamic diameter less than about 5 nanometers.
10. The process according to claim 1, further comprising the step adjusting said dispersion of nanoparticles to a pH within a suitable physiological condition.
11. The process according to claim 1, further comprising the step of administering to a patient a pharmaceutical composition comprising said dispersion of nanoparticles.
12. A nanoparticle dispersion comprising cerium oxide nanoparticles prepared according to the process of claim 1.
13. The nanoparticle dispersion of claim 12, wherein said cerium oxide nanoparticles are characterized by a cubic fluorite structure.
14. The nanoparticle dispersion of claim 12, wherein said cerium oxide nanoparticles are characterized by a hydrodynamic diameter less than about 5 nanometers.
15. A pharmaceutical composition comprising cerium oxide nanoparticles prepared according to the process of claim 1.

* * * * *